United States Patent
Flaig et al.

(10) Patent No.: US 9,321,820 B2
(45) Date of Patent: Apr. 26, 2016

(54) COMPOSITIONS AND METHODS FOR TREATING BLADDER CANCER

(75) Inventors: Thomas Flaig, Englewood, CO (US); Arthur E. Frankel, Temple, TX (US); Andrew Thorburn, Denver, CO (US); Michael L. Glode, Golden, CO (US)

(73) Assignees: The Regents of the University of Colorado, Denver, CO (US); Scott & White Healthcare, Temple, TX (US)

( * ) Notice: Subject to any disclaimer, the term of this patent is extended or adjusted under 35 U.S.C. 154(b) by 0 days.

(21) Appl. No.: 13/502,132

(22) PCT Filed: Oct. 14, 2010

(86) PCT No.: PCT/US2010/052634
§ 371 (c)(1),
(2), (4) Date: May 25, 2012

(87) PCT Pub. No.: WO2011/047135
PCT Pub. Date: Apr. 21, 2011

(65) Prior Publication Data
US 2012/0232010 A1  Sep. 13, 2012

Related U.S. Application Data

(60) Provisional application No. 61/251,676, filed on Oct. 14, 2009.

(51) Int. Cl.
*A61P 13/10* (2006.01)
*A61K 38/00* (2006.01)
*A61K 38/18* (2006.01)
*C07K 19/00* (2006.01)
*C07K 14/485* (2006.01)
*C07K 14/34* (2006.01)
*A61K 38/16* (2006.01)

(52) U.S. Cl.
CPC ............... *C07K 14/485* (2013.01); *A61K 38/16* (2013.01); *A61K 38/164* (2013.01); *A61K 38/1808* (2013.01); *C07K 14/34* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,616,482 A * | 4/1997 | Williams | 435/194 |
| 2006/0159708 A1 * | 7/2006 | Harrison et al. | 424/245.1 |
| 2007/0196366 A1 * | 8/2007 | Zangemeister-Wittke et al. | 424/141.1 |

FOREIGN PATENT DOCUMENTS

WO  WO 01/87982  * 11/2001

OTHER PUBLICATIONS

Shaw et al., J. Biol. Chem., 1991, vol. 266(31):21118-21124.*

* cited by examiner

*Primary Examiner* — Xiaozhen Xie
(74) *Attorney, Agent, or Firm* — Michael T. Wiwchar; Cochran Freund & Young, LLC

(57) ABSTRACT

The present invention provides methods and compositions for treating bladder cancer. In particular, the present invention provides a fusion protein comprising a toxin moiety that is linked to an epithelial growth factor (EGF) moiety. The toxin moiety and the EGF moiety can be linked optionally via a linker. Typically, the fusion protein is administered intravesically into the cancerous bladder.

7 Claims, 2 Drawing Sheets

COMPOSITIONS AND METHODS FOR TREATING BLADDER CANCER

CROSS-REFERENCE TO RELATED APPLICATIONS

This application claims the priority benefit of U.S. Provisional Application No. 61/251,676, filed Oct. 14, 2009, which is incorporated herein by reference in its entirety.

FIELD OF THE INVENTION

The present invention relates to treating bladder cancer using a fusion protein comprising a toxin moiety that is linked to an epithelial growth factor (EGF) moiety, optionally via a linker. Typically, the fusion protein is administered intravesically into the cancerous bladder.

BACKGROUND OF THE INVENTION

Bladder cancer is a common cancer with an estimated 67,160 new cases and 13,750 deaths in 2007. Most patients with non-muscle-invasive (superficial) cancers are initially treated with cystoscopic resection sometimes followed by intravesical therapy with *bacillus* Calmette-Guerin (BCG) solution. This solution contains live, weakened bacteria that stimulate the immune system to kill cancer cells in the bladder. The doctor will typically use a catheter to put the BCG solution in the bladder, and the patient needs to hold the solution in the bladder for at least about two hours. BCG bladder cancer treatment is usually done once a week for six weeks. BCG is a non-specific and irritating agent that has been in use for more than 30 years with little change. BCG lacks acceptable efficacy and has many side effects and limited tolerability. Some of the side-effects of BCG treatment include, but are not limited to, irritation of the bladder; an urgent need to urinate; the need to urinate frequently; pain, especially when urinating; fatigue; blood in the urine; nausea; a low-grade fever; and chills.

Moreover, many patients with non-invasive bladder cancer have a recurrence, with a recent meta-analysis reporting a recurrence rate of 39% after BCG therapy. In patients with high risk non-invasive bladder cancer, recurrence after intravesical BCG is very common with a recurrence rate in excess of 50%.

Accordingly, there is a need for effective non-invasive methods for treating bladder cancer.

SUMMARY OF THE INVENTION

Some aspects of the invention provide methods for treating bladder cancer in a subject. Such methods generally comprise administering a diphtheria toxin epidermal growth factor (DT-EGF) fusion protein directly to a cancerous bladder of the subject. Often the DT-EGF fusion protein is administered directly to cancerous cells of the bladder. Typically, the DT-EGF fusion protein is administered intravesically (i.e., directly instilled) into the cancerous bladder. The bladder is easily accessible via a fiberoptic cystoscope. For example, after the diagnosis of superficial bladder cancer, patients are regularly re-examined by cystoscope every 3-6 months for the first few years. Biopsies are routinely obtained via the cytsoscopy. Such methods can be used to instill DT-EGF fusion protein into the cancerous bladder.

In some embodiments, the amount of DT-EGF fusion protein administered ranges from about 500 ng/mL to about 2,000 ng/mL, and typically from about 500 ng/mL to about 1,500 ng/mL.

Methods for producing DT-EGF fusion proteins are known to one skilled in the art. However, most conventional methods utilize *E. coli* to produce DT-EGF fusion proteins, which can be difficult and results in DT-EGF fusion proteins that have limited stability. The Present inventors have found that many problems associated with using *E. coli* to produce DT-EGF fusion proteins, including limited stability of the resulting DT-EGF fusion protein, can be avoided by using *Pichia pastoris*. In order to produce DT-EGF in *P. pastoris*, the DNA encoding DT-EGF was modified to (a) introduce an N-terminal alanine, (b) optimize codon usage for efficient translation in *P. pastoris*, (c) abolish N-linked glycosylation sites, (d) optionally add a linker (e.g., $(G_4S)_3$ or $G_{10}$, where G is glycine and S is serine) between the DT and EGF moieties, and (e) add restriction sites for subcloning in the pPICZalpha yeast expression plasmid containing an alpha factor prepro leader sequence and the AOX1 promoter.

Some aspects of the invention thus provide DT-EGF fusion protein produced by *P. pastoris* using the modified DNA described herein as well as *P. pastoris* transfected with the modified DNA, vector comprising the modified DNA, and the modified DNA itself.

DETAILED DESCRIPTION OF THE INVENTION

Targeted toxins for use in chemotherapy are fusion proteins that combine a targeting molecule that selectively binds to and enters tumor cells with a toxin that kills the target cells. Clinical trials of targeted toxins directed against various tumors have led to FDA approval of denileukin diftitox (ONTAK), which is a fusion of diphtheria toxin (DT) and interleukin-2 (IL-2), for the treatment of cutaneous T cell lymphoma. Targeting is typically achieved with antibodies or growth factors that bind to tumor cell receptors. Toxins are often derived from bacterial pathogens (e.g. diphtheria toxin) or plants.

Epithelia growth factor receptor (EGFR) plays an important role in bladder cancer pathogenesis. It has been shown that bladder cancer cells express EGFR protein. In contrast, EGFR is quite uncommon in the normal (i.e., non-cancerous) bladder epithelial cells. Accordingly, the present inventors have discovered that bladder cancer can be effectively treated using a fusion protein comprising a toxin that is linked to an epithelial growth factor protein (EGF). In this manner, the selective binding of EGF by cancerous bladder epithelial cells allow selective administration of the toxin to cancerous bladder cells. The fusion proteins of the invention comprise a toxin moiety (e.g., DT toxin) linked to an EGF moiety (targeting moiety). In some embodiments, the toxin moiety is linked to the EGF moiety through a linker. Thus, some aspects of the invention provide a fusion protein where both toxin and EGF domains are produced from a recombinant construct. As the application provides the necessary information regarding the arrangement of toxin and antibody domains, and the sub regions within them, it will be recognized that any number or chemical coupling or recombinant DNA methods can be used to generate a fusion protein of the invention. Thus, reference to any particular fusion protein or a coupled toxin-EGF is not necessarily limiting.

The present invention will now be described in reference to diphtheria toxin (DT)-EGF fusion protein and methods for using the same to treat bladder cancer. However, it should be appreciated the scope of the invention is not limited to DT-EGF fusion protein as other toxin moieties can be used instead of DT moiety.

The DT-EGF fusion protein can be a fusion protein produced recombinantly. Alternatively, DT moiety and EGF moiety can be independently recombinantly produce and linked via chemically. Typically, however, DT-EGF fusion protein is recombinantly produced. The DT toxin moiety can be a truncated mutant or a wild type moiety, such as $DT_{390}$, $DT_{389}$, $DT_{383}$, $DT_{370}$, $DT_{388}$, or other truncated mutants, with and without point mutations or substitutions, as well as a full length toxin with point mutations. Thus, as just illustrative examples of the DT-EGF fusion protein, the invention provides $DT_{389}$-EGF, and $DT_{390}$-EGF fusion proteins. Derivatives of these fusion proteins can be designed and constructed by one skilled in the art given the disclosure of the present application.

The toxin moiety retains its toxic function. Often the toxin moiety also retains its membrane translocation function to the cytosol in full amounts. The loss in binding function located in the receptor binding domain of the protein (i.e., DT) diminishes systemic toxicity by reducing binding to non-target cells. Thus, the fusion proteins of the invention can be selectively and relatively safely administered. The routing function normally supplied by the toxin binding function is supplied by the EGF moiety. It should be appreciated that the EGF moiety includes at least a portion of the epitope that is recognized by EGFR of the bladder cancer cells.

Any EGF moiety that can be selectively recognized by the bladder cancer cells is effective with the toxin moiety, provided that the toxin achieves adequate proteolytic processing along this route. Adequate processing can be determined by the level of cell killing.

The recombinant fusion proteins of the invention can be produced from recombinant EGF moiety and recombinant DT moiety each containing a single unpaired cysteine residue. An advantage of this method is that DT moiety and EGF moiety are easily produced and properly folded using a variety of bacteria or other cells. For chemically coupled DT-EGF fusion protein, one or more amino acids (e.g., glycine, serine, or any combination thereof) can is inserted between the DT moiety and the EGF moiety. However, typically the fusion proteins of the invention are produced recombinantly. Such recombinant production of the fusion proteins of the invention can include optionally inserting a linker by modifying the plasmid construct that is used for recombinant production of fusion proteins.

Some methods of the invention use $DAB_{389}$EGF. $DAB_{389}$EGF is a toxic fusion protein of diphtheria toxin and the epidermal growth factor (EGF) in which the domain recognized by the diphtheria toxin (DT) receptor (e.g., DT domain amino acids 391-535) is replaced with EGF, so that the targeted toxin is recognized by the native epidermal growth factor receptor (EGFR). Superficial bladder cancer commonly expresses EGFR whereas the normal bladder lining does not. Superficial bladder cancer frequently recurs after initial treatment, with these recurrent cases potentially leading to cystectomy (surgical removal of the bladder) or advanced disease. Some methods of the invention utilize the accessibility of superficial bladder cancer to direct treatment. Such methods include instillation of DT-EGF into the bladder to selectively target cancerous bladder cells.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

DT-EGF was initially produced by *E. coli*. However the production in *E. coli* was difficult to prepare and had limited stability. Repeated efforts to standardize refolding from bacterial inclusions gave poor yields and purity. To overcome these problems, DT-resistant proprietary *Pichia pastoris* strains and modified gene expression plasmids was used. In order to produce DT-EGF in *P. pastoris*, the DNA encoding DT-EGF was modified to (a) introduce an N-terminal alanine, (b) optimize codon usage for efficient translation in *P. pastoris*, (c) abolish N-linked glycosylation sites, and optionally (d) add a $(G_4S)_3$ or $G_{10}$ (where G is glycine and S is serine) linker between the DT and EGF moieties. The plasmid DNA was transformed into a DT-resistant *P. pastoris* strain (JW107: a wild type DT resistant strain; $Mut^+$, $DT^R$, $Ura3^+$, $His4^+$). Using this transformant, fermentation and purification procedures were developed. After 24 hr induction, an average expression level of 18.5 mg/L was obtained. DT-EGF in culture supernatant was purified by a series of chromatography such as (1) Butyl-650M hydrophobic interaction column step, (2) Poros 50 HQ anion exchange column step, (3) Phenyl HP hydrophobic interaction column step, (4) Butyl-650M hydrophobic interaction column step, and (5) Q HP anion exchange column step. Its final yield was 30% (5.6 mg/L). The final preparation had >98% of purity, <0.04% aggregates, and 6.0 μM of IC50 to an EGFR1 bladder cancer cell line.

DT-EGF Gene Construction

An intermediate vector named "A-dmDTop390-bisFv (G4S) in pET" and the pnPICZalpha vector (Woo et al., Protein Expr Purif., 2002, 25, 270-282, which is incorporated herein by reference in its entirety) were used to construct an expression vector having the DT-EGF gene.

The EGF gene was amplified using two primers, 5'NcoI-EGF (5'-TTCTTGCCATGGAACAGCGATAGCGAATGCCCG-3' SEQ ID NO: 1) and 3'E-st-EGF (5'-CGTGAATTCTTAGCGCAGTTCCCACCATTTCAG-3' SEQ ID NO:

2). PCR was performed for 30 cycles at the following conditions: 1 cycle at 94° C. for 2 min, 30 cycles of 94° C. for 30 sec followed by 55° C. for 30 sec and then 72° C. for 80 sec, and 1 cycle of 72° C. for 7 min. PCR products were analyzed by 1% agarose gel electrophoresis containing 40 µg of ethidium bromide (EtBr, BioRad) per 100 mL of 1% agarose (Gibco). DNA fragments with correct size were excised from the agarose gel and purified using Qiagen gel extraction kit.

The amplified EGF gene was digested with NcoI and EcoRI restriction enzymes. The intermediate vector was also digested with NcoI, EcoRI and calf intestine phosphatase. A large DNA fragment of ~4 kbp was isolated and purified. The large DNA fragment and the digested EGF gene were ligated and transformed into E. coli NovaBlue competent cells. A new construct named "A-dmDTop390-bisFv(G4S)-EGF in pET" was obtained.

Figure 1:
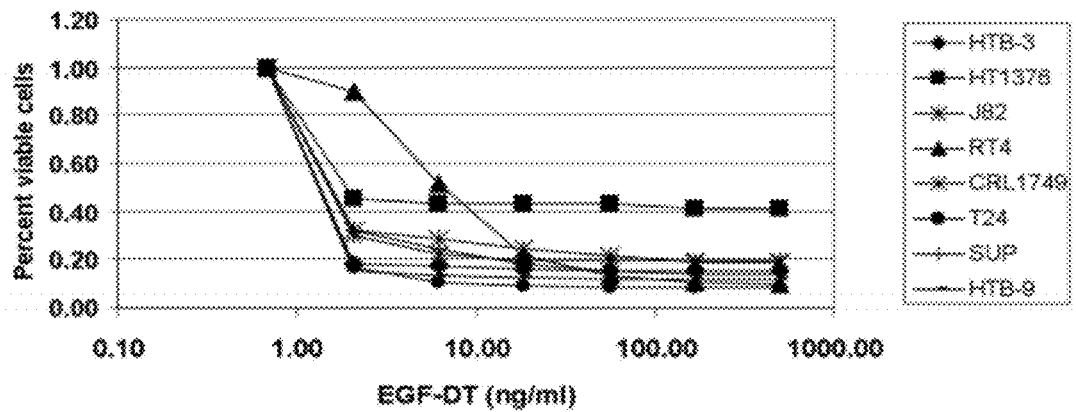
FIG. 1 is a graph showing the percentages of surviving bladder cancer cells 72 hours after treatment with DT-EGF fusion protein at various concentrations.
Figure 2:
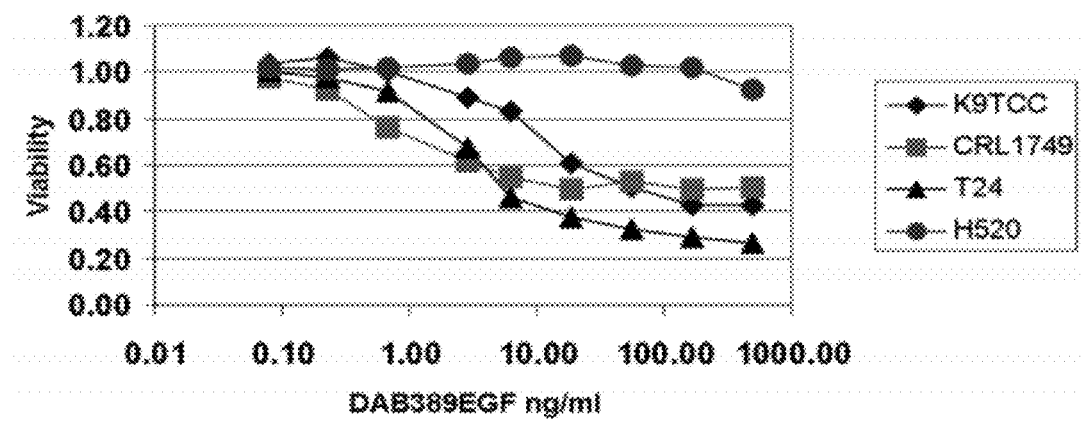
FIG. 2 is a graph showing the results of the specificity of DT-EGF for cells that express the receptor of EGF.

The above new construct was digested with XhoI and EcoRI enzymes in order to obtain a DNA fragment, "X-A-DT390-EGF-E". The X-A-DT390-EGF-E fragment was inserted between XhoI and EcoRI sites of the pnPICZalpha vector. The resulting vector, "X-A-DT390-EGF-E in pnPIC-Zalpha" was transformed into a DT resistant strain (JW107). Ten µg of plasmid DNA was linearized with SadI and then electroporated into the JW107 strain utilizing 20052, 7500V/cm and 25 μF with a Bio-Rad GenePulser (Bio-Rad Laboratories). Transformants expressing zeocin markers were obtained by spreading onto the zeocin agar plate. Six single colonies from each transformation were grown in 5 ml of YPD medium (1% yeast extract, 2% peptone and 2% dextrose) in 14 ml test tubes for 2 days to obtain a saturated cell density and then resuspended in 3 ml of BMMYC medium (1% yeast extract, 2% peptone, 100 mM potassium phosphate, pH 7.0, 1.34% yeast nitrogen base without amino acids, $4\times10^{-5}$% biotin, 0.5% methanol and 1% casamino acids) for induction. About 15 μL of methanol was supplemented every 24 hours after initiation of methanol induction. The supernatants were harvested after 2 days of methanol induction and then subjected to SDS-PAGE or Western blotting to check the DT-EGF expression level. Finally, DT-EGF expression *Pichia pastoris* strain was obtained. This DT-EGF fusion protein has an N-terminal alanine; no N-linked glycosylation site and a restriction site for subcloning in the pnPICZa yeast expression plasmid containing an alpha factor prepro leader sequence and the AOX1 promoter.

Fermentation

In some instances, the expression of pDT-EGF (i.e., expression of DT-EGF by *P. pastoris*) was optimized by tuning fermentation procedure below. *Pichia pastoris* transformed with pnPICZalpha-DT-EGF was maintained as frozen stocks at −80° C. in 25% (w/v) glycerol. One mL of frozen stocks was inoculated into 50 mL YSG broth (1% yeast extract, 2% soytone peptone, 2% glycerol) and cultivated for two days at 28° C. at 250 rpm. Twelve mL from these cultures were inoculated into 250 mL YSG broth in a 1-L flask and cultured for one day at 28° C. at 250 rpm. Cultures were then be used as the second seed cultures for inoculation of 4 L of complex fermentation medium—2% yeast extract, 2% soytone peptone, 4% glycerol, 1.34% yeast nitrogen base with ammonium sulfate but without amino acids (Difco), and 0.04% foam away (Invitrogen). The fermentations were done in a BioFlo 110 fermentor (New Brunswick Scientific) with a methanol sensor and controller (Raven Biotechnology) to maintain methanol at set concentrations during induction. The fermentor was linked to a computer running AFS BioCommand Windows-based software. After consumption of glycerol detected by a spike in dissolved oxygen, there was a 75% glycerol feed for 7 hours (0.1 to 3 grams/min) and then methanol induction controlled to maintain methanol at 0.15%. Dissolved oxygen was maintained at >25% by adding oxygen as needed. The pH was maintained at 6.5 during fermentation by adding 29% $NH_4OH$ or 40% $H_3PO4$ as needed. Temperature was set at 28° C. for growth and ramped down to 15° C. during the first four hours of methanol induction and then maintained at 15° C. Optimal induction time was 24 hours. After 24 hr induction, an average expression level of 18.5 mg/L was obtained.

Purification

Purification procedure was developed to obtain DT-EGF with >98% purity. The purification procedure includes (1) Butyl-650M hydrophobic interaction column step, (2) Poros 50 HQ anion exchange column step, (3) Phenyl HP hydrophobic interaction column step, (4) Butyl-650M hydrophobic interaction column step, and (5) Q HP anion exchange column step. Its final yield was 30% (5.6 mg/L).

Characterization of the DT-EGF Preparation

In order to characterize the DT-EGF preparations during process development and confirm the feasibility of the tuned production procedure, the following procedures were performed: (a) protein aggregate analysis by size exclusion, (b) SDS-PAGE analysis, (c) measurement of DT-EGF concentration, (d) potency assay, and (e) endotoxin assay test. The final preparation had >98% of purity, <0.04% aggregates, 6.0 μM of IC50 to an EGFR1 bladder cancer cell line and <5.0 EU/mg of DT-EGF.

In Vivo Tests of DT-EGF Treatment

Human bladder cancer cells (HTB9) were infected with lentivirus containing the firefly luciferase gene (HTB9-luc), allowing for the non-invasive monitoring of the implanted cells. For tumor implantation, 6-8 week old female nu/nu mice were anesthetized and their bladder catheterized with a 24 gauge plastic catheter, instilling 100 μL of $1.5\times10^6$ HTB9-luc cells. The cells were held in the bladder for 3 hours by a retention suture temporarily placed around the urethra. Treatment was pursued only in mice with implantation of the HTB9-luc cells confirmed by the presence of luciferase activity 1 week after the implantation procedure. $DAB_{389}$EGF was given in the active treatment group and $DAB_{388}$GMCSF in the control arm, with 70 ng of drug administered twice weekly for 2 weeks in 70 μL of solution. The drug was retained in the bladder for 2 hours in an analogous manner to the implantation procedure, using a temporary retention suture under anesthesia. A total of 6 mice were treated in each group. In those receiving $DAB_{389}$EGF, 5 of 6 had complete loss of luciferase activity after 2 weeks of intravesical therapy. One of these 6 mice had reduction in luciferase activity, but a low level of residual activity persisted after the 2 week treatment period. In contrast, luciferase activity persisted in 5 of 6 mice in the $DAB_{388}$GMCSF control arm at 2 weeks.

Results and Discussion

The present inventors have discovered and demonstrated effectiveness of DT-EGF in treating bladder cancer. The activity of DT-EGF was assessed in vitro to determine if exposing bladder cancer cells to DT-EGF would be lethal. As shown in FIG. 1, more than half of the bladder cancer cells were killed or suppressed when exposed to DT-EGF for 72 hours. The specificity of DT-EGF was also assessed. While many clinically used targeted agents in oncology require strong reliance to a particular molecular pathway to be effective, without being bound by any theory it is believed that DT-EGF merely requires a threshold level of intact EGF receptors to be effective. When the receptor is present, it allows DT-EGF to enter the cell where the DT or diphtheria toxin portion kills the cells. To test the specificity of DT-EGF for cells that express the receptor of EGF, a lung cancer cell line (H520) that does not express EGF receptor was included along with the bladder cancer cells. As shown in FIG. 2, H520 was not affected by DT-EGF at doses 5-10 times the effective dose in multiple tested bladder cancer cell lines (note the X axis is logarithmic, to capture this large dose range). Without being bound by any theory, it is believed that this result is indicative that DT-EGF was exerting a specific killing action based on the presence of the EGF receptor, rather than a non-specific toxicity to any cell.

Figure 3:
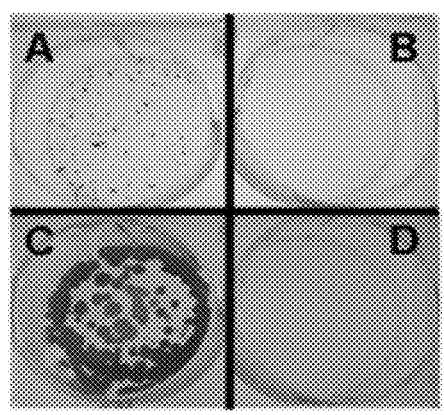
FIG. 3 shows the effect of DT-EGF to suppress the formation of colony of bladder cancer (clonogenic assay) utilizing a treatment or exposure time of 2 hours. Panel A shows bladder cancer cell line HT1376 colonization with no treatment after 2 hours. Panel B shows the result of treating the same with 25 ng/mL of DT-EGF after 2 hours. Panel C shows the result of bladder cancer cell colonization at 24 hours with no treatment. Pane D shows the result of bladder cancer cell colonization at 24 hours after treatment with 25 ng/mL of DT-EGF.

The practical considerations of delivering this drug to patients with bladder cancer was considered. Generally, it is difficult for patients to "hold in" intravesical agents in the bladder for more than 1-2 hours. Consider that in addition to the volume of DT-EGF or other therapeutic agent instilled in the human bladder, the kidneys continue to produce urine and fill up the bladder. Therefore, the effect of DT-EGF to suppress the formation of colony of bladder cancer (clonogenic assay) was determined utilizing a treatment or exposure time of 2 hours. As shown in FIG. 3, the strong clonogenic suppression (i.e., prevention of the formation of new cancer cell colonies) with a single 2 hour treatment time was clearly observed. This showed that a 1-2 hour treatment time in humans is suitable.

Figure 4:
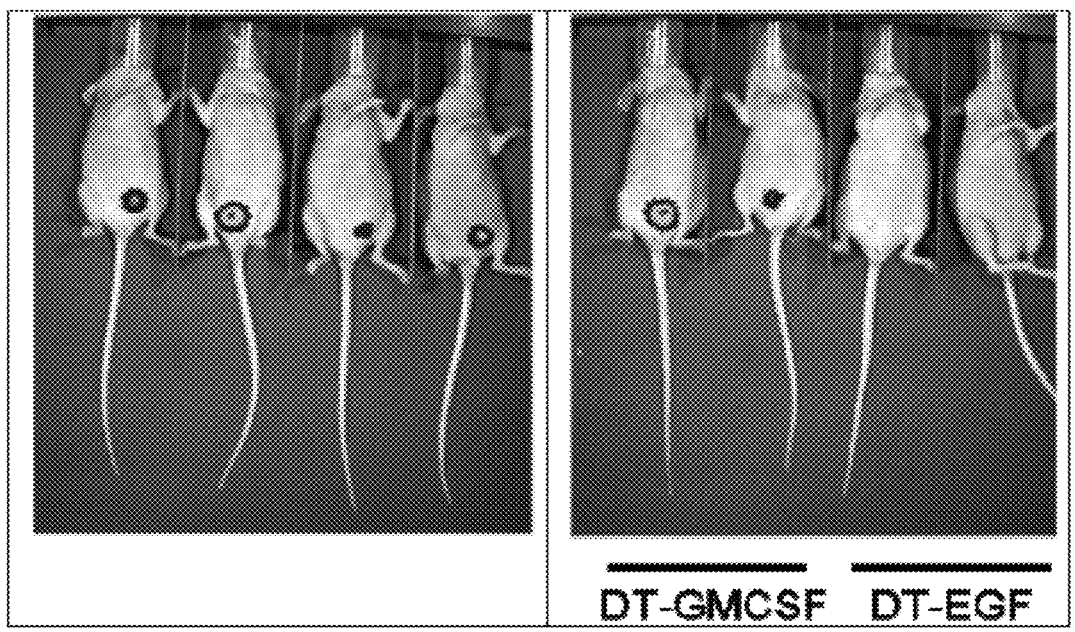
FIG. 4 shows results of not treating and treating mice that were implanted with bladder cancer cells. Panel A shows the mice seven days after having been implanted with human bladder cancer cells. Panel B shows the mice two weeks after first DT-EGF treatment (two mice on the right), and DT-GMCSF treated mice (two mice on the left).

Animal testing of DT-EGF for bladder cancer was also performed. This involved a mouse (athymic) bladder cancer model in which the tumor grows in the outer layers of the bladder (orthotopic) and the tumor was engineered so that its presence can be followed with luciferase activity. In the first cohort of mice treated with intravesical DT-EGF, no change in luciferase activity was observed after 1 week; however, there was a loss in luciferase activity in the mice treated with DT-EGF at 2 weeks, but no change in the activity of mice treated with DT-GMCSF, which was used as a control. See FIG. 4. The pathology review demonstrated no noticeable residual tumor in the DT-EGF treated mice, but as expected gross tumor was observed in the DT-GMCSF treated mice. These data showed the efficacy, deliverability, and specificity of this treatment approach for the treatment of bladder cancer.

Figure 5:
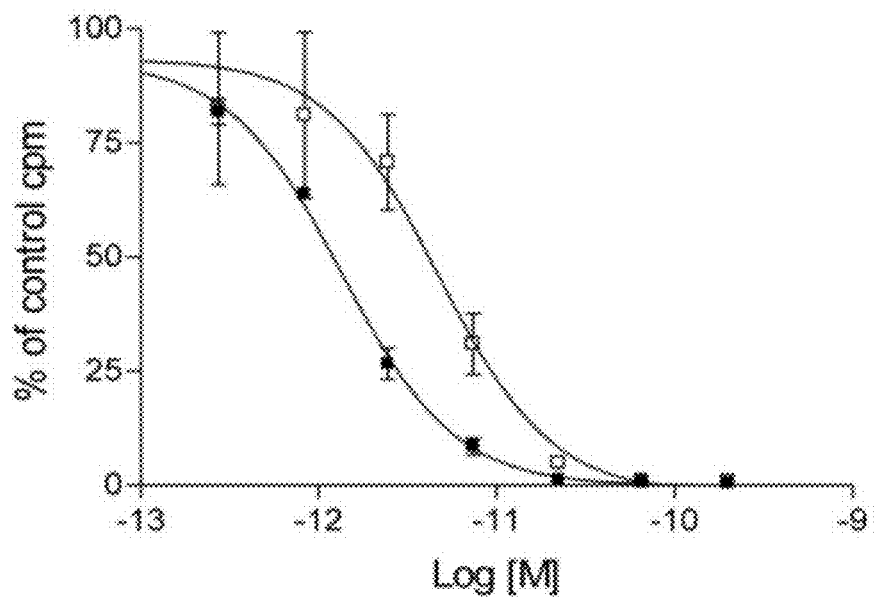
FIG. 5 shows the results of cytotoxicity assay on U373MG cells after 50 h incubation with dilutions of Bacterial DT-EGF (bDT-EGF) or *Pichia* DT-EGF (pDT-EGF). One microcurie 3H-thymidine added for 18 h then harvest on glass fiber mats and counted in LKB Betaplate reader. □-bDT-EGF ($IC_{50}$=4.7 µM). ■-pDT-EGF ($IC_{50}$=1.4 µM).

As stated above, the present inventors have discovered methods for treating bladder cancer using DT-EGF. In one particular example, 50 mg of DT-EGF is prepared and provided to bladder cancer subjects. The present inventors prepared DT-EGF in *Pichia pastoris* because DT-EGF produced by *E. coli* was difficult to prepare and had limited stability. Repeated efforts to standardize refolding from bacterial inclusions gave poor yields and purity. In order to produce DT-EGF in *P. pastoris*, the present inventors have modified the DNA encoding DT-EGF to (a) introduce an N-terminal alanine, (b) optimize codon usage for efficient translation in *P. pastoris*, (c) abolish N-linked glycosylation sites, (d) optionally add a linker (e.g., $(G_4S)_3$ or $G_{10}$) between the DT and EGF moieties, and (e) add restriction sites for subcloning in the pnPICZalpha yeast expression plasmid containing an alpha factor prepro leader sequence and the AOX1 promoter. A diphtheria toxin resistant *P. pastoris* strain, JW107 ($DT^R$, Mut+, His4+, Ura3+), was transformed and selected on zeocin selection media. Recombinant protein expression was induced with methanol and partially purified by hydrophobic interaction and anion exchange chromatography. Protein molecular weight and purity were evaluated by SDS-PAGE. Cytotoxic potency was improved relative to bacterial DT-EGF (FIG. 5).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

What is claimed is:

1. A method for treating bladder cancer in a subject, said method comprising administering a pharmaceutically acceptable formulation of a diphtheria toxin-epidermal growth factor (DT-EGF) fusion protein chosen from $DT_{390}$-EGF, $DT_{389}$-EGF, $DT_{383}$-EGF, $DT_{370}$-EGF, and $DT_{388}$-EGF to a subject with bladder cancer and in need of bladder cancer treatment,
   wherein the DT-EGF formulation is administered intravesically and retained in the bladder for approximately 1-2 hours.

2. The method of claim 1, wherein the amount of administered DT-EGF fusion protein is about 50 mg.

3. The method of claim 1, wherein the subject is a mammal.

4. The method of claim 3, wherein the subject is a human.

5. The method of claim 1, wherein the bladder cancer is superficial bladder cancer.

6. The method of claim 1, wherein the DT-EGF formulation is retained in the bladder for approximately 2 hours.

7. The method of claim 1, wherein the DT-EGF fusion protein of the DT-EGF formulation comprises:
   an N-terminal alanine; and
   no N-linked glycosylation site.

* * * * *

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: 5'NcoI-EGF

<400> SEQUENCE: 1
ttcttgccat ggaacagcga tagcgaatgc ccg                    33

<210> SEQ ID NO 2
<211> LENGTH: 33
<212> TYPE: DNA
<213> ORGANISM: Artificial Sequence
<220> FEATURE:
<223> OTHER INFORMATION: 3'-E-st-EGF

<400> SEQUENCE: 2
cgtgaattct tagcgcagtt cccaccattt cag                    33